United States Patent
Andersen et al.

(10) Patent No.: US 6,558,653 B2
(45) Date of Patent: May 6, 2003

(54) METHODS FOR TREATING PERIODONTAL DISEASE

(76) Inventors: Scot N. Andersen, 13002 S. Mountain Crest Cir., Draper, UT (US) 84020; Jimmy B. Wilson, 1401 E. Vestry Cir., Draper, UT (US) 84020

( * ) Notice: Subject to any disclaimer, the term of this patent is extended or adjusted under 35 U.S.C. 154(b) by 0 days.

(21) Appl. No.: 09/956,539

(22) Filed: Sep. 19, 2001

(65) Prior Publication Data

US 2003/0059379 A1 Mar. 27, 2003

(51) Int. Cl.[7] .............................. A61D 5/00; A61C 3/00; A61K 7/16; A61B 17/32; A61L 5/00
(52) U.S. Cl. ........................ 424/49; 433/215; 433/216
(58) Field of Search .................... 424/49, 58; 514/900; 433/215, 216

(56) References Cited

U.S. PATENT DOCUMENTS

| | | | | |
|---|---|---|---|---|
| 3,900,034 A | * | 8/1975 | Katz et al. ................. | 128/395 |
| 4,336,809 A | * | 6/1982 | Clark ........................ | 128/665 |
| 5,090,908 A | | 2/1992 | Teumim-Stone ............ | 433/215 |
| 5,123,902 A | * | 6/1992 | Muller et al. ................. | 604/21 |
| 5,230,621 A | | 7/1993 | Jacoby ........................ | 433/29 |
| 5,292,253 A | | 3/1994 | Levy ........................ | 433/215 |
| 5,570,182 A | | 10/1996 | Nathel et al. ............... | 356/345 |
| 5,611,793 A | | 3/1997 | Wilson et al. ................ | 606/2 |
| 5,642,997 A | * | 7/1997 | Gregg et al. ................ | 433/215 |
| 5,720,304 A | | 2/1998 | Omura ....................... | 128/898 |
| 5,795,153 A | * | 8/1998 | Rezhmann ................. | 433/215 |
| 5,925,036 A | * | 7/1999 | Maxwell ..................... | 606/13 |
| 5,941,701 A | | 8/1999 | Moran et al. ................. | 433/1 |
| 5,957,691 A | * | 9/1999 | Goodman et al. .......... | 433/215 |
| 5,968,035 A | * | 10/1999 | Goodman et al. .......... | 433/215 |
| 5,968,036 A | * | 10/1999 | Goodman et al. .......... | 433/215 |
| 6,019,605 A | | 2/2000 | Myers ........................ | 433/215 |
| 6,039,565 A | | 3/2000 | Chou et al. ................... | 433/29 |
| 6,086,363 A | | 7/2000 | Moran et al. ................. | 433/1 |
| 6,290,496 B1 | * | 9/2001 | Azar et al. ................. | 433/216 |
| 6,391,283 B1 | * | 5/2002 | Jensen et al. ................ | 424/49 |
| 6,462,070 B1 | * | 10/2002 | Hansan et al. .............. | 514/410 |

OTHER PUBLICATIONS

*Periodontal Therapy You and Your Patients Won't Fear . . . Laser ENAP*, Millennium Dental Technologiers, Inc.
*Questions & Answers, PerioChip 2.5 MG (chlorhexidine gluconate) Delivers Measurable Outcomes*, ASTRA Pharmaceuticals, L.P., pp. 1–14, 1998.
*Porphyomonas Gingivalis Genome Project*, Collaboration between FDC and TIGR, funded by NIDR, http://www.forsyth.org/pggp/significancel.htm; Sep. 1, 1999.
Finkbeiner, R. Larry, D.D.S., M.S., *The Results of 1328 Periodontal Pockets Treated with the Argon Laser: Selected Pocket Thermolysis*, Journal of Clinical Laser Medicine & Surgery, vol. 13, No. 4, pp. 273–281, Nov. 4, 1995.
Gregg, Robert H., D.D.S. and McCarthy, Delwin K., D.D.S., *Laser ENAP for Periodontal Bone Regeneration*, Dentistry Today, vol. 17, No. 5, 4 pgs., May 1998.
Gregg, Robert H., D.D.S. and McCarthy, Delwin K., D.D.S., *Laser ENAP for Periodontal Liagment (PDL) Regeneration*, Dentistry Today, vol. 17, No. 11, 3 pgs., Nov. 1998.
Haas, R.; Dortbudak, O.; Mensdorff–Pouilly, N.; and Mailath, G., *Elimination of Bacteria on Different Implant Surfaces through Photosensitization and Soft Laser. An In Vitro Study*, Published by Department of Oral Surgery, School of Dentistry, University of Vienna, Austria, Feb. 13, 2001.
Jeffocat, Marjorie K. et al., *Adjunctive Use of a Subgingival Controlled Release Chlorhexidine Chip Reduces Probing Depth and Improves Attachment Level Compared with Scaling and Root Planning Alone*, J. Periodontal, pp. 989–997, Sep. 1998.
Rovaldi, CR; Piegvsky, A.; Sole, NA; Friden, PM; Rothstein, DM; and Spacciapoli, P., *Photoactive Porphyrin Derivative with Broad–Spectrum Activity Against Oral Pathogens In Vitro*, Published by Periodontix, Inc., Watertown, Massachuetts 02472, Feb. 13, 2001.
Sarka, S. and Wilson, M., *Lethal Photosensitization of Bacteria in Subgingival Plaque from Patients with Chronic Periodontitis*, Published by Department of Microbiology, Institute of Dental Surgery, London, England, Feb. 13, 2001.
Soukos, NS.; Wilson, M.; Burns, T.; and Speight, PM, *Photodynamic Effects of Toluidine Blue on Human Oral Keratinocytes and Fibroblasts and Streptococcus Sanguis Evaluated In Vitro*, Published by Department of Oral Pathology, Eastman Dental Institute, London, United Kingdom, Feb. 13, 2001.
Soukos, NS; Ximenez–Fyvie, LA; Hamblin, MR; Socransky, SS; and Hasan, T., *Targeted Antimicrobial Photochemotherpy*, Published by Wellman Laboratories of Photomedicine, Department of Dermatology, Massachusetts General Hospital, Harvard medicine School, Boston, Massachusetts 02114–2698, Feb. 13, 2001.
Wilson, Michael, *Bactericidal Effect of Laser Light and Its Potential Use in the Treatment of Plaque–Related Diseases*, International Dental Journal (1994), 44, pp. 181–189.

* cited by examiner

Primary Examiner—Shep K. Rose
(74) Attorney, Agent, or Firm—Workman, Nydegger & Seeley

(57) ABSTRACT

Methods for treating periodontal disease and other diseased tissues that utilize a dye composition and laser energy. The laser energy (typically about 450 nm to about 600 nm) heats and destroys the diseased tissue and bacteria, while the dye composition causes the laser energy to be selectively absorbed by the targeted tissue. An argon gas laser that emits blue-green light may be used in conjunction with a red-orange dye that strongly absorbs light energy emitted by the argon gas laser. An 810 diode laser may be used in conjunction with the argon laser in order to provide additional heating properties.

20 Claims, 1 Drawing Sheet

METHODS FOR TREATING PERIODONTAL DISEASE

BACKGROUND OF THE INVENTION

1. The Field of the Invention

The present invention relates generally to methods for treating periodontal disease, particularly to methods that utilize laser energy to destroy necrotic tissue and bacteria that have been stained with an appropriate dye.

2. The Relevant Technology

It is well known that periodontal disease is caused by bacteria that grows and festers within the periodontal pocket. Porphyromonas gingivalis and other bacteria host not only in the soft tissue around the periodontal pocket, but also in plaque that is formed on the surface of the tooth. If left untreated, such bacteria can cause swelling of the gingiva, pain and possible loss of the tooth. Surrounding gums and teeth can also become infected.

In the conventional treatment of periodontal disease, instruments are inserted into the periodontal pocket to mechanically debride the plaque from the tooth and also to remove the necrotic soft tissue by curettage. Antibiotics may also be conventionally placed in the periodontal pocket following conventional treatment to ensure complete eradication of the infection and to combat reinfection.

Even with conventional debridement and curettage of the periodontal pocket, it is well known that subsequent bacterial infections of the periodontal pocket following treatment are common and can recur relatively soon after treatment. This is particularly true since the patient may not exercise proper dental care following the treatment for the periodontal disease. Consequently, such subsequent bacterial reinfection of the periodontal pocket may often necessitate further debridement of hard and soft tissue from the periodontal pocket.

Chemical therapies have also been used to treat periodontitis and other infections of the periodontal pocket. Such treatments require the application of high concentrations of an antimicrobial agent for hours or days. The drawback of chemical therapies is that they do not result in the physical removal of necrotic and infectious tissues and have not been shown to completely heal the problem area. They cannot remediate the problem of detached gingiva and cannot eliminate the presence of the periodontal pocket. In addition, bacterial strains can develop resistance to chemical antibiotics, and their use can disrupt the microflora of the oral cavity and the gastrointestinal tract, leading to secondary infections by opportunistic microbials.

In extreme cases, periodontal flap surgery has been used, but this technique involves cutting, cleaning, sewing, and reattaching the gingival tissue to the tooth surface. This technique is highly invasive, expensive, and painful, and requires considerable time to heal.

More recently, less intrusive techniques involving the use of lasers have been developed, although such processes can damage surrounding gum and hard tissue in an effort to completely remove the infecting bacteria and diseased tissue. In general, laser techniques are not sufficiently selective and the laser equipment can be quite expensive. One such technique, as taught by U.S. Pat. No. 6,019,605 to Myers, involves irradiation of the soft tissue and plaque with high power laser light, followed by conventional debridement and curettage of the periodontal pocket, followed by reirradiating the tissue and plaque with high power laser light.

Another laser technique, as taught by U.S. Pat. No. 5,611,793 to Wilson, involves the application of a photosensitizing compound to the infected area such that the infecting bacteria are stained by the compound and then irradiating the area with laser light at a wave length absorbed by the photosensitizing compound in order to destroy the infecting bacteria. One drawback of Wilson is that Wilson only discloses the use of lasers that emit wavelengths at the red end of the spectrum or longer, some of which are quite expensive. Longer wavelengths have been found to penetrate deeply into tissue, with the result being that their exclusive use can result in damage to surrounding or underlying tissues. Increased pain and a slower recovery may result from the use of such lasers. Another drawback is that some of the photosensitizing compounds disclosed in Wilson are known to be carcinogenic or otherwise harmful.

In view of the foregoing, it would be an advancement in the art to provide new photosensitizing compositions and lasers for use in treating periodontal disease that addressed the foregoing drawbacks. In particular, it would be an advancement to provide lower cost lasers that could be used to treat periodontal disease. In would be an additional advancement to provide lasers that emitted at appropriate wavelengths in order to limit the depth of penetration of the laser energy in order to better focus and restrict the tissue-destroying action of the laser energy. In would yet be an advancement in the art to provide photosensitizing compositions that maximized the absorption of the improved lasers of the present invention, particularly if such compositions were not carcinogenic or dangerous to use.

Methods which utilize photosensitizing compositions and lasers in treating periodontal disease are disclosed and claimed herein.

SUMMARY OF THE INVENTION

The present invention involves methods for treating periodontal disease in the periodontal pocket by destroying the infecting bacteria and removing necrotic tissue with less pain, less risk of damage to surrounding tissues, and lower cost compared to the prior art. Such methods involve the use of appropriate dye compositions in order to stain the infecting bacteria and necrotic tissue. Stained tissues much more readily absorb the light energy emitted by the laser. This allows for the efficient and accurate thermal destruction, disinfecting and ablation of the bacteria and necrotic tissue by means of laser energy.

In brief, contacting the infected and surrounding necrotic tissues with a staining dye system treats and prepares the targeted tissue and bacteria within the periodontal pocket for the laser irradiation step. The targeted tissues and bacteria absorb the dye, thus becoming stained and sensitized to the laser's output wavelength(s). A laser that outputs one or more wavelengths absorbed by the dye system is then used to irradiate the stained area. The targeted tissues are thereby destroyed and the infecting bacteria killed as the stained issue more strongly absorbs the energy contained within the laser light compared to surrounding tissues that are not stained. Absorption of the laser energy causes the stained tissue and bacteria to quickly heat up and vaporize and/or become denatured and detached from the surrounding healthy tissues so as to form a coagulate and/or char.

In a preferred composition according to the invention, the dye composition includes a red-orange water-based dye within a carrier liquid. The dye composition may optionally include one or more antibiotics, anesthetics, flavorants, or additional dye components. In the preferred method of the invention, a laser that strongly emits in the blue-green region of the spectrum is used in combination with the preferred dye composition, preferably by means of a fiber optic strand or tip that carries the laser light energy to the target site. An example of such a laser is an argon laser. Of course it will readily be understood that the use of any laser that strongly emits one or more wavelengths of light in a range of about 450 nm to about 600 nm is within the scope of the invention.

Because of the dye composition's light absorption characteristics, it absorbs the laser light, which selectively heats and destroys the stained bacteria and surrounding necrotic tissue, thus forming a coagulate and/or char. The coagulate or char formed by the procedure is removed as it adheres to the fiber tip of the laser by simply removing and cleaning the fiber tip as needed. Depending on the size of the diseased area, it may be necessary to remove and insert the fiber tip a number of times in order to remove all of the coagulate or char formed during destruction of the bacteria and necrotic tissue. Removal and insertion of the fiber tip may also serve to score (i.e., damage) the freshly exposed tissue, thus stimulating growth and readhesion of the tissue to the tooth.

The argon or other laser emitting in a range of about 450 nm to about 600 nm may either be used alone or in combination with a laser diode that emits in the IR region (e.g., 810 nm) in order to provide additional and complementary heating characteristics. In the case where a dual or multi-wavelength system is employed, it may be advantageous to include a dye system that includes two or more dyes that are able to collectively absorb each of the wavelengths being emitted. In the case where a multi-wavelength laser device is used that emits in the IR region, it may be useful to include one or more naphthalocyanines, which absorb strongly in the 750–850 nm range.

The use of the dye composition to target certain areas within the periodontal pocket results in a lower laser power requirement to kill the infecting bacteria (as compared to the prior art) because the formula enhances the absorption characteristics of the infected tissue at the wavelength of the laser. In addition, the relatively shorter wavelengths (i.e., high frequencies) of light emitted in the region of about 450 nm to about 600 nm penetrate less deeply into tissue compared to laser energy at longer wavelengths, thereby further pinpointing the tissue-destroying activity of the laser energy. Because of the lower laser power requirement, as well as the more focused tissue-destroying effect using the laser energy disclosed herein, there is less risk of damage to surrounding soft and hard tissue, less pain during and after surgery, and healing of the gingival tissue occurs faster than it otherwise would. In addition, the controlled damage that does occur to surrounding tissue is beneficial because the use of the laser on the infected soft tissue creates a new adjacent soft tissue surface that can readhere to the tooth, thereby closing the periodontal pocket. Furthermore, the preferred photosensitizing formula is not carcinogenic or otherwise harmful to the patient.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

I. INTRODUCTION

Figure 1:
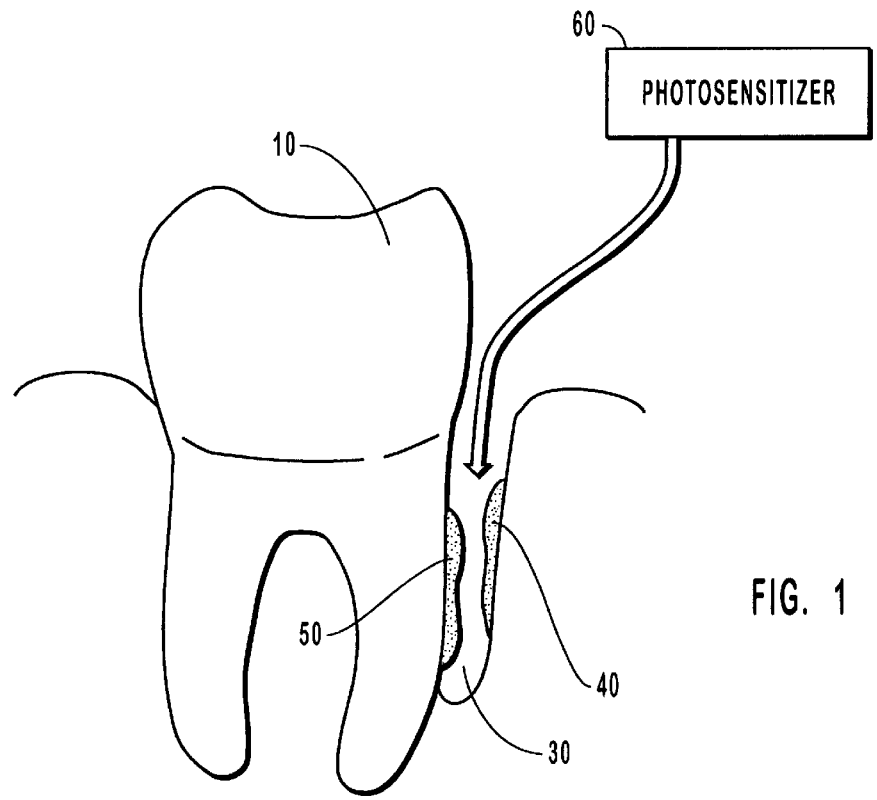
FIG. 1 is a diagrammatic view illustrating application of the photosensitizer to the diseased periodontal pocket.

The present invention encompasses methods for treating periodontal disease and other bacteria-caused infections or lesions. The methods involve the staining of bacteria and necrotic tissue with a staining dye formulation to render the stained area more susceptible to thermal destruction by laser energy. Thereafter, the stained area is irradiated with laser energy in order to selectively heat and destroy the stained area.

The use of laser energy at predominately shorter wavelengths (e.g., from an argon or 532 laser) results in a more focused destruction of the diseased tissue. This is because shorter wavelength (i.e., higher frequency) light penetrates less deeply into the tissue compared to longer wavelengths (i.e., lower frequencies), such as those disclosed in U.S. Pat. No. 5,611,793 to Wilson. Nevertheless, for purposes of broadly teaching the use of laser energy to destroy bacteria that have been treated with a photosensitizing composition or dye, the foregoing patent is incorporated herein by reference.

The term "targeted tissue", for purposes of disclosure and the appended claims, shall encompass bacteria, necrotic tissue and any other tissue or entity within a periodontal pocket that is to be destroyed using the methods described herein.

II. LASERS

An important feature of the present invention is the use of laser energy to heat and destroy bacteria and surrounding necrotic tissue within a diseased periodontal pocket. In general, at least a portion of the laser energy utilized within the inventive methods disclosed herein will include light having a wavelength in a range of about 450 nm to about 600 nm, more preferably in a range of about 460 nm to about 550 nm, and most preferably in a range of about 480 nm to about 520 nm. The most preferred wavelengths (i.e., about 480 nm to about 520 nm) are in the blue to blue-green color range.

One presently preferred laser that is able to emit laser energy within the foregoing ranges is an argon gas laser (or argon ion laser). An example of a suitable argon laser is the ACCUCURE ELITE, which is manufactured by LaserMed, Inc., located in West Jordan, Utah. Another is the DENTAL 300, manufactured by HGM Medical Laser Systems, Inc., located in Salt Lake City, Utah. In general, argon gas lasers emit various wavelengths of light that are predominantly in a range from 488 nm to 514.5 nm, with the blue-green color defined as 514.5 nm light being the predominant wavelength emitted.

In addition to argon gas lasers, other lasers that emit light within a wavelength range of about 450 nm to about 600 nm include diode pumped 532 nm lasers known as the ELITE and the ELITE ULTRA, also available from HGM Medical Laser Systems.

In addition to the use of laser energy in a range of about 450 nm to about 600 nm, it is within the scope of the invention to utilize laser energy in the IR region as a supplemental source of laser energy in order to provide certain desired functions or properties. For example, it may be desirable in some cases to supplement to the laser energy emitted by an argon gas laser (or other appropriate laser) with laser energy emitted by an 810 diode laser. The use of laser energy having a wavelength of 810 nm is desirable, for example, because certain organisms are known to naturally strongly absorb light energy at this wavelength. In addition, 810 diode lasers are useful for soft tissue debridement. An example of a suitable 810 diode laser is the AURORA Diode Laser System available from Premier Laser Systems, Inc. Other IR lasers that emit in the region of 800–980 nm include the DIOLASE ST, sold by American Dental Technologies, Inc., located in Corpus Christi, Tex.; the TWILITE Diode Laser, available from Biolase Technology, Inc., located in San Clemente, Calif.; and the CERALAS D15, which is sold by CeramOptec, Inc., located in East Longmeadow, Mass.

The use of laser energy that is of a relatively shorter wavelength and higher frequency provides advantages over laser energy that is of a longer wavelength and lower frequency. For example, longer wavelength laser energy penetrates far more deeply into tissue before it begins to heat the tissue, compared to shorter wavelengths. The result is that longer wavelength light is less able to focus the tissue-destroying effect within a desired area. Moreover, because the energy penetrates more deeply, more energy and time is required to heat a given area. Hence, the use of laser energy of a shorter wavelength significantly reduces both the time and energy required to heat a given area of tissue. Moreover, because such heat is less diffuse it is also more focused, which provides more precise heating of the targeted area. Finally, both the argon gas laser and the 810 diode laser are much less expensive compared to many other lasers presently available in the market, such as $CO_2$, HeNe, Yag 1064 lasers, and the like.

III. DYES AND DYE COMPOSITIONS

The purpose of the dye compositions is to stain targeted bacteria and tissue so that they will selectively absorb the emitted laser energy and become selectively heated and destroyed compared to the surrounding non-stained tissues. Selectively staining the bacteria and necrotic tissue greatly increases the efficiency of the tissue destroying activity of the laser energy because the stained tissue heats up and is destroyed much more rapidly than the non-stained tissue. Accordingly, the use of dyes greatly decreases the time and energy necessary to heat a given area of tissue. Moreover, reducing the intensity and/or duration of laser energy irradiation provides a zone of safety that prevents or reduces the inadvertent destruction of healthy tissue.

The dye compositions for use in the methods according to the invention may include any dye or combination of dyes that increase the tendency of the stained bacteria and other targeted tissue to absorb the laser energy being applied to the targeted tissue. In general, any dye that is able to absorb light energy at a wavelength within a range of about 450 nm to about 600 nm is within the scope of the invention. Examples include red, orange and yellow dyes, as well as dye colors intermediate to red and orange, and intermediate to orange and yellow. Hence, the whole spectrum of contemplated dyes are between reddish dyes, at one end, and yellowish dyes, at the other end.

In one embodiment of the invention, the dye composition will include a red-orange water-based dye within a carrier liquid. Examples of useful dyes include FD&C Red #40, FD&C Red #28, Red fuschin, FD&C Yellow #5 Lake, FD&C Yellow #6 Lake, carotene, carotenoids, Eosin Y, acradine orange, safranin, and violet. Eosin Y can preferentially be absorbed by bacteria and necrotic tissue, but not healthy soft tissue, at a pH of 5.5.

In addition, in the case where longer wavelength laser energy is used in combination with the preferred shorter wavelength laser energy, one or more additional dyes that are able to absorb such longer wavelengths may also be included. In the case where it is desired to use an 810 nm diode laser, for example, it may be desirable to use one or more naphthalocyanines, which absorb strongly in the 750–850 nm range. Examples of useful naphthalocyanines include, but are not limited to, tetra-t-butylnaphthalocyanine; naphthalocyanine, bis(tribenzylsiloxy)silicon; naphthalocyanine, bis(trihexylsiloxy)tin; naphthalocyanine, bis(trihexyloxysiloxy)silicon; naphthalocyanine, bis(triisobutylsiloxy)silicon; naphthalocyanine, 1,6,10,15,19,24,28,33-octabutoxy-, palladium(II); naphthalocyanine, 2.11,20,29-tetrakis(1,1-dimethylethyl)- ; naphthalocyanine, 1,10,19,28-tetraphenyl-, hydroxyaluminum(III); naphthalocyanine, trihexylsiloxyaluminum; and naphthalocyanine, trihexylsiloxygallium.

The dyes will preferably be dispersed within a carrier liquid. Examples of suitable liquids that may be included within the carrier liquid include at least one of water, ethanol, other alcohols, glycerin, propylene glycol, polypropylene glycol, polyethylene glycol, and other polyols.

The dye compositions may optionally include other active or inactive components including, but not limited to, antibiotics, anesthetics, and flavorants. Examples of useful antibiotic or antimicrobial agents include, but are not limited to, chlorhexidine gluconate, triclosan, cetyl pyridinium chloride, cetyl pyridinium bromide, benzalkonium chloride, tetracycline, methyl benzoate, and propyl benzoate.

Examples of useful anesthetic agents include, but are not limited to, benzocaine, lidocaine, tetracaine, butacaine, dyclonine, pramoxine, dibucaine, cocaine, and hydrochlorides of the foregoing.

Suitable flavorants include, but are not limited to, at least one of peppermint oil, sodium saccharine, aspartame, oil of wintergreen, oil of spearmint, strawberry favoring, and grape flavoring.

EXAMPLE 1

A dye composition for use in the methods according to the invention was made that included the following components:

| | |
|---|---|
| Chlorhexidine Gluconate | 0.12% |
| Ethanol | 30% |
| Sodium Saccharin | 0.5% |
| D&C Red #40 | 0.5% |
| Peppermint Oil | 0.5% |
| Polyethylene Glycol 20,000 | 20% |
| Water | 46.38% |
| Benzocaine | 2% |

EXAMPLE 2

A dye composition for use in the methods according to the invention was made that included the following components:

| Water      | 99.5% |
|------------|-------|
| D&C Red #28 | 0.5%  |

EXAMPLE 3

A dye composition for use in the methods according to the invention was made that included the following components:

| Water                  | 79.38% |
|------------------------|--------|
| Red Fuschin            | 0.5%   |
| Chlorhexidine Gluconate | 0.12%  |
| Ethanol                | 20%    |

EXAMPLE 4

A dye composition for use in the methods according to the invention was made that included the following components:

| Water                  | 78.88% |
|------------------------|--------|
| D&C Red #40            | 0.5%   |
| Ethanol                | 20%    |
| Chlorhexidine Gluconate | 0.12%  |
| Peppermint Oil         | 0.5%   |

IV. METHODS FOR TREATING PERIODONTAL DISEASE

Figure 2:
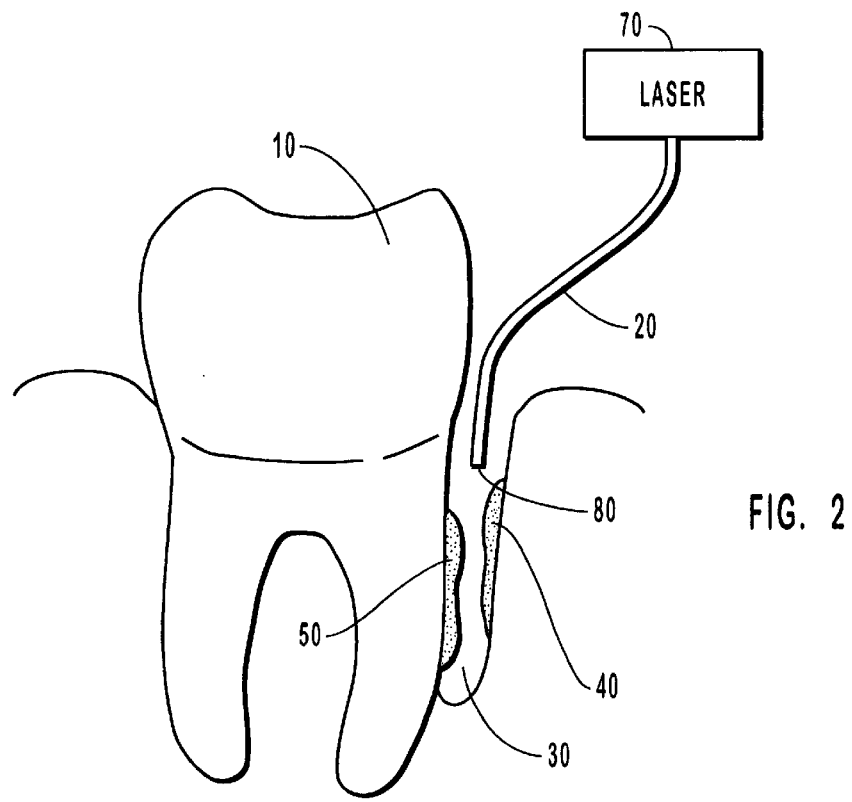
FIG. 2 is a diagrammatic view illustrating irradiation of the diseased periodontal pocket by laser.

The preferred embodiment of the method for treating periodontal disease is described in conjunction with FIG. 2. With reference first to FIG. 1, a periodontal pocket 30 next to a patient's tooth 10 is therein illustrated. The periodontal pocket 30 includes both diseased soft tissue 40 as well as plaque 50 attached to the tooth 10. Both the diseased soft tissue 40 and the plaque 50 form hosts for bacteria of the type causing periodontal disease.

In order to treat the periodontal disease, a staining dye composition 60 is applied to the diseased soft tissue 40 and plaque 50 within the periodontal pocket 30. The dye composition 60 can also be used to irrigate the periodontal pocket 30 during laser irradiation. The dye composition is a fluid that preferably selectively adheres to the diseased soft tissue 40 as well as the plaque 50.

With reference to FIG. 2, the same periodontal pocket 30 next to the same patient's tooth 10 is therein illustrated. Here the diseased soft tissue 40 and plaque 50 have been stained by the dye composition 60. A free end of an optical fiber 80 is inserted into the periodontal pocket 30. A laser 70 is optically connected to the other end of the optical fiber 20 so that upon activation, the laser 70 emits laser radiation through the optical fiber 20 and against both the stained plaque 50 and diseased soft tissue 40 contained within the periodontal pocket 30. In one embodiment, the laser is a combination Argon/810 diode laser, which emits radiation at dual primary wavelengths of 514.5 nm and 810 nm.

The laser energy is absorbed by the stained soft tissue 40 and plaque 50. Absorption of the laser energy causes the stained soft tissue 40 and plaque 50 to rapidly heat up, which kills the infecting bacteria. The heat also causes the infected tissue 40 and plaque 50 to coagulate and/or char. The coagulated or charred necrotic material is removed by adhering to the fiber 20 and fiber tip 80. Fiber 20 is removed, cleaned, reinserted, and the laser is fired again. The process is continued until the diseased soft tissue 40 and plaque 50 have all been removed.

Insertion and removal of the laser fiber tip 80 may also score the underlying healthy gingival tissue as it cuts, thereby creating a fresh surface of raw tissue. After the diseased soft tissue 40 and plaque 50 have been removed, the fresh surface of raw tissue resulting from the heating and scoring process is prone to more readily adhere to the tooth 10 surface than tissue that has not been traumatized. Adhesion of the raw tissue to the tooth 10 closes the periodontal pocket 30.

Because of the dye composition's light absorption characteristics, tissues stained therewith selectively absorb the laser light instead of non-stained tissues, which selectively heats and destroys the stained bacteria and surrounding necrotic tissue. In the case where a dual or multi-wavelength system is employed, it may be advantageous to include a dye system that includes two or more dyes that are able to collectively absorb each of the wavelengths being emitted.

The use of the dye composition to target certain areas within the periodontal pocket results in a lower laser power requirement to kill the infecting bacteria (as compared to the prior art) because the formula enhances the absorption characteristics of the infected tissue at the wavelength of the laser. In addition, the relatively shorter wavelengths (i.e., high frequencies) of light emitted in the region of about 450 nm to about 600 nm penetrate less deeply into tissue compared to laser energy at longer wavelengths, thereby further pinpointing the tissue-destroying activity of the laser energy. Because of the lower laser power requirement, as well as the more focused tissue-destroying effect using the laser energy disclosed herein, there is less risk of damage to surrounding soft and hard tissue, less pain during and after surgery, and accelerated healing of the gingival tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for treating periodontal disease in a periodontal pocket, comprising:

applying a dye composition to targeted bacteria and tissue within a periodontal pocket, said dye composition including at least one dye that absorbs light energy comprising at least one wavelength in a range of about 450 nm to about 600 nm; and irradiating said periodontal pocket with laser energy comprising at least one wavelength in a range of about 450 nm to about 600 nm.

2. A method for treating periodontal disease as defined in claim 1, wherein said dye composition comprises at least one dye selected from the group consisting of red dyes, orange dyes, yellow dyes, dyes having a color intermediate to red and orange, and dyes having a color intermediate to orange and yellow.

3. A method for treating periodontal disease as defined in claim 1, wherein said dye composition comprises at least one of FD&C red #40, FD&C red #28, red fuschin, FD&C yellow #5 lake, FD&C yellow #6 lake, carotene, carotenoids, Eosin Y, acradine orange, safranin, or violet.

4. A method for treating periodontal disease as defined in claim 1, wherein the dye composition further comprises at least one antibiotic.

5. A method for treating periodontal disease as defined in claim 4, wherein the antibiotic comprises at least one of chlorhexidine gluconate, triclosan, cetyl pyridinium chloride, cetyl pyridinium bromide, benzalkonium chloride, tetracycline, methyl benzoate, or propyl benzoate.

6. A method for treating periodontal disease as defined in claim 1, wherein the dye composition further comprises at least one anesthetic.

7. A method for treating periodontal disease as defined in claim 6, wherein the anesthetic comprises at least one of benzocaine, lidocaine, tetracaine, butacaine, dyclonine, pramoxine, dibucaine, cocaine, or a hydrochloride thereof.

8. A method for treating periodontal disease as defined in claim 1, wherein the dye composition further comprises at least one flavorant.

9. A method for treating periodontal disease as defined in claim 8, wherein the flavorant comprises at least one of peppermint oil, sodium saccharine, aspartame, oil of wintergreen, oil of spearmint, strawberry favoring, or grape flavoring.

10. A method for treating periodontal disease as defined in claim 1, wherein said laser energy is produced by an argon laser that primarily emits at least one wavelength in a range from about of 488 to about 515 nm.

11. A method for treating periodontal disease as defined in claim 1, wherein said laser energy further includes infra red light.

12. A method for treating periodontal disease as defined in claim 11, wherein said infra red light is emitted by a laser diode that primarily emits at 810 nm.

13. A method for treating periodontal disease as defined in claim 12, wherein said dye composition further includes at least one dye that absorbs infra red light.

14. A method for treating periodontal disease as defined in claim 12, wherein said dye composition further includes at least one naphthalocyanine.

15. A method for treating periodontal disease as defined in claim 14, wherein said naphthalocyanine includes at least one of tetra-t-butylnaphthalocyanine; naphthalocyanine, bis (tribenzylsiloxy)silicon; naphthalocyanine, bis (trihexylsiloxy)tin; naphthalocyanine, bis (trihexyloxysiloxy)silicon; naphthalocyanine, bis (triisobutylsiloxy)silicon; naphthalocyanine, 1,6,10,15,19, 24,28,33-octabutoxy-, palladium(II); naphthalocyanine, 2,11,20,29-tetrakis(1,1-dimethylethyl)-; naphthalocyanine, 1,10,19,28-tetraphenyl-, hydroxyaluminum(III); naphthalocyanine, trihexylsiloxyaluminum; or naphthalocyanine, trihexylsiloxygallium.

16. A method for treating periodontal disease in a periodontal pocket, comprising:

applying a dye composition to targeted bacteria and tissue within a periodontal pocket, said dye composition comprising (i) at least one dye that absorbs light energy comprising at least one wavelength in a range of about 450 nm to about 600 nm and (ii) at least one of an antibiotic, an anesthetic, or a flavorant; and irradiating said periodontal pocket with laser energy comprising at least one wavelength in a range of about 450 nm to about 600 nm.

17. A method for treating periodontal disease as defined in claim 16, wherein said dye composition comprises at least one dye selected from the group consisting of red dyes, orange dyes, yellow dyes, dyes having a color intermediate to red and orange, and dyes having a color intermediate to orange and yellow.

18. A method for treating periodontal disease as defined in claim 16, wherein said laser energy further includes infra red light and wherein said dye composition further includes at least one dye that absorbs infra red light.

19. A method for treating periodontal disease in a periodontal pocket, comprising:

applying a dye composition to targeted bacteria and tissue within a periodontal pocket, said dye composition comprising (i) at least one dye that absorbs light energy and (ii) at least one of an antibiotic or an anesthetic; and irradiating said periodontal pocket with laser energy that comprising at least one wavelength absorbed by the dye composition.

20. A method for treating periodontal disease as defined in claim 19, wherein said dye composition includes at least one dye that absorbs light energy comprising at least one wavelength in a range of about 450 nm to about 600 nm, wherein said laser energy comprises at least one wavelength in a range of about 450 nm to about 600 nm.

* * * * *

UNITED STATES PATENT AND TRADEMARK OFFICE
CERTIFICATE OF CORRECTION

PATENT NO. : 6,558,653 B2
DATED : May 6, 2003
INVENTOR(S) : Scot N. Andersen and Jimmy B. Wilson It is certified that error appears in the above-identified patent and that said Letters Patent is hereby corrected as shown below:

Column 5,
Line 18, change "regionof" to -- region of --

Column 6,
Line 49, change "favoring" to -- flavoring --

Column 9,
Line 30, change "favoring" to -- flavoring --

Column 10,
Line 39, delete "that"

Signed and Sealed this

Twenty-third Day of December, 2003

JAMES E. ROGAN
*Director of the United States Patent and Trademark Office*